US008526669B2

(12) United States Patent
Lavin et al.

(10) Patent No.: US 8,526,669 B2
(45) Date of Patent: Sep. 3, 2013

(54) METHOD FOR MULTIPLE IMAGE PARAMETER ADJUSTMENT BASED ON SINGLE USER INPUT

(75) Inventors: Brent Jason Lavin, Wauwatosa, WI (US); Menachem Halmann, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 339 days.

(21) Appl. No.: 12/906,703

(22) Filed: Oct. 18, 2010

(65) Prior Publication Data
US 2012/0092527 A1  Apr. 19, 2012

(51) Int. Cl.
*A61B 8/00* (2006.01)
(52) U.S. Cl.
USPC .......................... 382/100; 600/437; 348/239
(58) Field of Classification Search
None
See application file for complete search history.

(56) References Cited

U.S. PATENT DOCUMENTS

| 5,919,138 | A | 7/1999 | Ustuner |
| 6,430,428 | B1 * | 8/2002 | Lindstedt ................ 600/410 |
| 2004/0015079 | A1 * | 1/2004 | Berger et al. ............ 600/437 |

* cited by examiner

*Primary Examiner* — Stephen R Koziol
*Assistant Examiner* — Raphael Schwartz
(74) *Attorney, Agent, or Firm* — McAndrews, Held & Malloy, Ltd.; Jacob Groethe; David Bates

(57) ABSTRACT

Systems and methods for determining scan parameters to be used during image acquisition are provided. Values of imaging effects can be input using user controls accessible from a user interface. A processor can determine scan parameters to be used during image acquisition based on the input imaging effect values. The determined scan parameters can be displayed using the user interface. Values of imaging effects and potential ranges of values of imaging effects can be constrained based on selected values of other imaging effects. Imaging effects can include image resolution, image penetration, frame rate and/or color flow sensitivity. Scan parameters can include: line density, number of focal zones, frequency, dynamic range, pulse repetition frequency, and/or number of compounding angles. An ultrasound imaging system can be used to acquire images using the determined scan parameters.

11 Claims, 5 Drawing Sheets

METHOD FOR MULTIPLE IMAGE PARAMETER ADJUSTMENT BASED ON SINGLE USER INPUT

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Embodiments of the present technology generally relate to determining scan parameters to be used during two-dimensional ("2D") and/or three dimensional ("3D") image acquisition. Certain embodiments provide for determining scan parameters to be used by an ultrasound imaging system during image acquisition.

Numerous scan parameters that can affect image quality are used by an ultrasound imaging system during image acquisition. Such scan parameters can include, for example: line density, number of focal zones, frequency, dynamic range, pulse repetition frequency, number of compounding angles, etc. Developing the skills required to effectively adjust multiple scan parameters to achieve a desired imaging effect can be a challenge to users, especially new users.

Thus, there is a need for improved systems and methods that provide for determining scan parameters to be used during image acquisition.

BRIEF SUMMARY OF THE INVENTION

Certain embodiments of the present technology provide systems, methods and non-transitory computer readable mediums encoded with instructions for determining scan parameters to be used during image acquisition.

In an embodiment, for example, a method for determining scan parameters to be used during image acquisition includes: receiving a first value for a first imaging effect, the first value being input using a first user control that is adjustable using a user interface; and using a computer processor to determine a plurality of scan parameters based on the first value, the determined plurality of scan parameters to be used when acquiring an image using an image acquisition device.

In an embodiment, for example, the plurality of scan parameters includes one or more of the following: line density, number of focal zones, frequency, dynamic range, pulse repetition frequency, number of compounding angles.

In an embodiment, for example, the first imaging effect is one of the following: image resolution, image penetration, frame rate or color flow sensitivity.

In an embodiment, for example, a method also includes displaying the determined plurality of scan parameters using the user interface.

In an embodiment, for example, a method also includes receiving a second value for a second imaging effect, the second value being input using a second user control that is adjustable using the user interface, and wherein the computer processor uses the first value and the second value to determine the plurality of scan parameters.

In an embodiment, for example, a method also includes: using the computer processor to determine a range of potential values for a second imaging effect based on the first value; and using the user interface to constrain a second user control that is adjustable using the user interface such that only values within the range of potential values for the second imaging effect can be input using the second user control.

In an embodiment, for example, a method also includes: using the computer processor to determine a range of potential values for a third imaging effect based on the first value and a second value input using the second user control; and using the user interface to constrain a third user control that is adjustable using the user interface such that only values within the range of potential values for the third imaging effect can be input using the third user control.

In an embodiment, for example, a method also includes: using the computer processor to determine a value for a second imaging effect based on the first value.

In an embodiment, for example, a method also includes: using the computer processor to determine a value for a third imaging effect based on the first value.

In an embodiment, for example, a method also includes: using the computer processor to determine a range of potential values for the second imaging effect based on the first value; using the computer processor to determine a range of potential values for the third imaging effect based on the first value; using the user interface to constrain a second user control that is adjustable using the user interface such that only values within the range of potential values for the second imaging effect can be input using the second user control; and using the user interface to constrain a third user control that is adjustable using the user interface such that only values within the range of potential values for the third imaging effect can be input using the third user control.

In an embodiment, for example, a system for determining scan parameters to be used during image acquisition includes: a computer processor configured to receive a first value for a first imaging effect, the first value being input using a first user control that is adjustable using a user interface that is operably connected to the computer processor, the computer processor configured to determine a plurality of scan parameters based on the first value, the determined plurality of scan parameters to be used when acquiring an image using an image acquisition device.

In an embodiment, for example, the plurality of scan parameters includes one or more of the following: line density, number of focal zones, frequency, dynamic range, pulse repetition frequency, number of compounding angles.

In an embodiment, for example, the first imaging effect is one of the following: image resolution, image penetration, frame rate or color flow sensitivity.

In an embodiment, for example, the image acquisition device is an ultrasound imaging system.

In an embodiment, for example, the computer processor is configured to receive a second value for a second imaging effect, the second value being input using a second user control that is adjustable using the user interface, and the computer processor is configured to use the first value and the second value to determine the plurality of scan parameters.

In an embodiment, for example, the computer processor is configured to determine a range of potential values for a second imaging effect based on the first value, and the computer processor is configured to use the user interface to constrain a second user control that is adjustable using the user interface such that only values within the range of potential values for the second imaging effect can be input using the second user control.

In an embodiment, for example, the computer processor is configured to determine a range of potential values for a third imaging effect based on the first value and a second value input using the second user control, and the computer processor is configured to use the user interface to constrain a third user control that is adjustable using the user interface such that only values within the range of potential values for the third imaging effect can be input using the third user control.

In an embodiment, for example, the computer processor is configured to determine a value for a second imaging effect based on the first value, and the computer processor is configured to determine a value for a third imaging effect based on the first value.

In an embodiment, for example, the computer processor is configured to determine a range of potential values for a second imaging effect based on the first value, the computer processor is configured to determine a range of potential values for a third imaging effect based on the first value, the computer processor is configured to use the user interface to constrain a second user control that is adjustable using the user interface such that only values within the range of potential values for the second imaging effect can be input using the second user control, and the computer processor is configured to use the user interface to constrain a third user control that is adjustable using the user interface such that only values within the range of potential values for the third imaging effect can be input using the third user control.

In an embodiment, for example, a non-transitory computer-readable storage medium encoded with a set of instructions for execution on a processing device and associated processing logic, wherein the set of instructions includes: a first routine configured to receive a first value for a first imaging effect, the first value being input using a first user control that is adjustable using a user interface, a second routine configured to determine a plurality of scan parameters based on the first value, the determined plurality of scan parameters to be used when acquiring an image using an image acquisition device.

Figure 1:
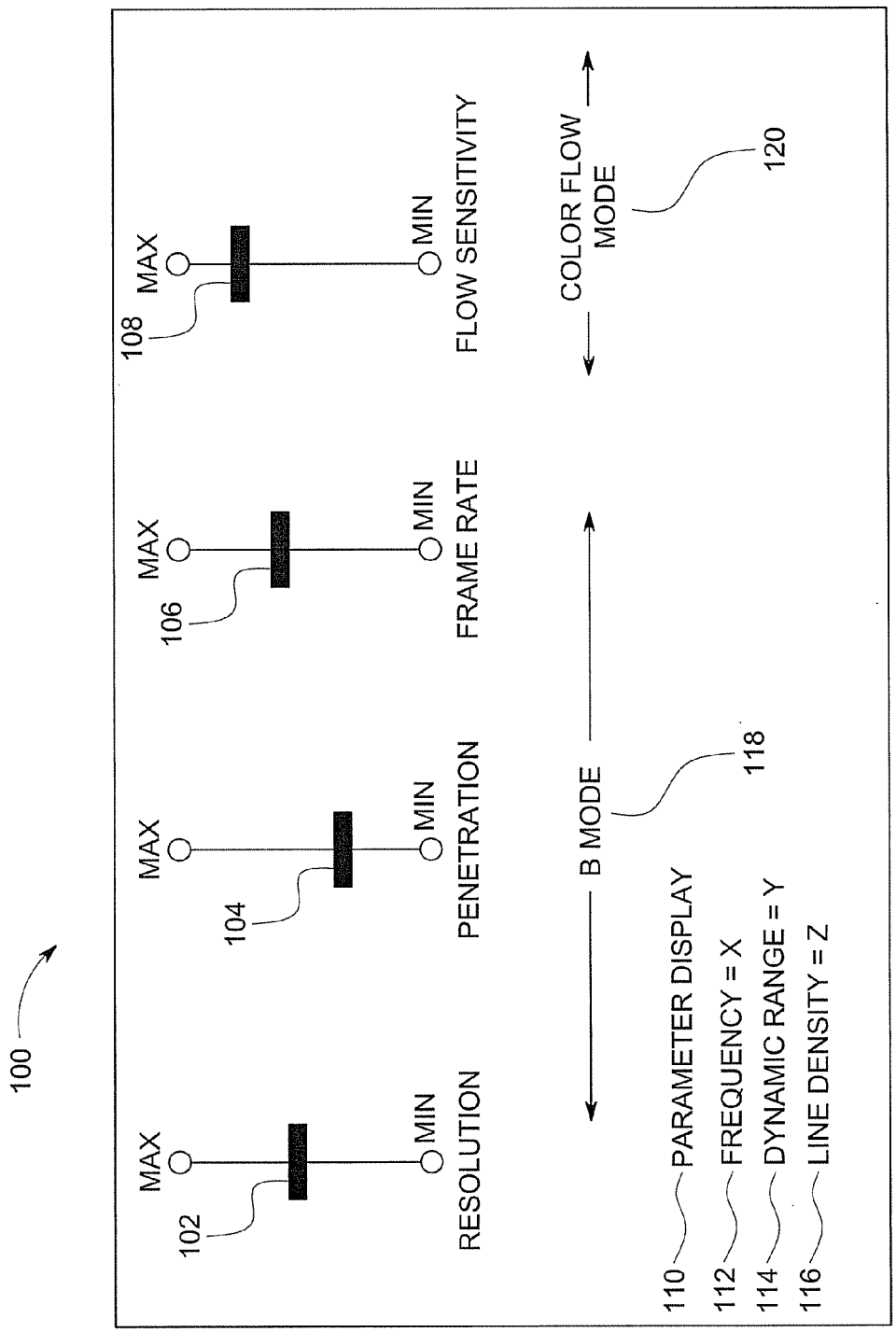
FIG. 1 illustrates a user interface panel used in accordance with an embodiment of the present technology.

The foregoing summary, as well as the following detailed description of embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

Embodiments of the present technology generally relate to determining scan parameters to be used during two-dimensional ("2D") and/or three dimensional ("3D") image acquisition. Certain embodiments provide for determining scan parameters to be used by an ultrasound imaging system during image acquisition.

While certain embodiments are discussed in connection with ultrasound imaging systems that acquire images as 2D frames, the inventions disclosed herein are not limited to such applications. The inventions herein can be used in connection with any image acquisition device where it is desirable to determine multiple image acquisition parameters to be used during image acquisition. For example, certain embodiments can be used in connection with 3D imaging systems and probes that acquire imaging data sets for 3D volumes.

It has been found that effective determination of multiple scan parameters to achieve a desired imaging effect during ultrasound imaging is generally not intuitive to users, especially those that are new. Such scan parameters can include, for example: line density, number of focal zones, frequency, dynamic range, pulse repetition frequency, number of compounding angles, etc.

Although a user may not know what a suitable scan parameter is for a desired imaging effect, the user should know what imaging effect they would like to achieve. For example, when operating an ultrasound imaging system in B-mode, a user should know whether they would like to increase or decrease: image resolution, which controls the amount of image detail that is captured; image penetration, which controls the depth at which an image is acquired; frame rate, which controls the frequency at which unique consecutive images are acquired. Also, when operating an ultrasound imaging system in color flow mode, a user should also know whether they would like to increase or decrease color flow sensitivity.

In order to achieve increased or decreased image resolution, image penetration, frame rate and/or flow sensitivity, multiple underlying scan parameters can be adjusted, such as line density, number of focal zones, frequency, dynamic range, pulse repetition frequency, number of compounding angles, etc.

Thus, it has been found that providing user controls that allow for adjustment of imaging effects (e.g., image resolution, image penetration, frame rate and/or color flow sensitivity) rather than relying solely on controls that allow for adjustment of underlying scan parameters, can provide for improved usability of ultrasound imaging systems.

Image resolution, image penetration, frame rate and color flow sensitivity are related such that a change in one may limit the possible range of another and/or require that the value of another be changed. For example, when increasing image resolution, image penetration and image frame rate are generally decreased, while color flow sensitivity is generally increased. For example, when increasing image penetration, image resolution, image frame rate and color flow sensitivity are generally decreased. For example, when increasing image frame rate, image resolution, image penetration and color flow sensitivity are generally decreased. For example, when increasing color flow sensitivity, image penetration and image frame rate are generally decreased, while image resolution is generally increased. Thus, it has been found that when the value of one of the imaging effects is set, the potential range of values for the remaining imaging effects can be determined and/or the values of remaining imaging effects can be set accordingly.

In certain embodiments, a system can provide a default setting for imaging effects and scan parameters. User controls associated with the imaging effects can be used to change one or more imaging effects, thereby changing the associated scan parameters. In an embodiment, the user controls are provided via a graphical user interface. Each user control can be bounded to reflect a maximum and minimum value for the imaging effect under present settings. The boundaries can be a determined initially by optimizing scan parameters to provide the maximum and minimum for each imaging effect. Each time a value of one of the imaging effects is changed, the scan parameters and values of the remaining imaging effects can be updated to reflect the change. Also, each time a value of one of the imaging effects is changed, the boundaries for the remaining imaging effects can be updated to reflect the change. In other words, the maximum and minimum for each imaging effect can be recalculated based on optimized scan parameters that are recalculated each time one of the imaging effect values is adjusted. This can update the boundaries for the imaging effects.

Embodiments of the present technology therefore provide user controls that can be used to adjust imaging effects (e.g., image resolution, image penetration, frame rate and/or color flow sensitivity), thereby automatically selecting scan parameters (e.g., line density, number of focal zones, frequency, dynamic range, pulse repetition frequency, number of compounding angles, etc.), automatically updating remaining imaging effects and/or automatically updating boundaries for remaining imaging effects. Certain embodiments provide for displaying selected scan parameters.

As described below, such user controls can be implemented in connection with a user interface of an ultrasound imaging system, for example. In certain embodiments, adjustment of such user controls can be reflected in an image provided on a display in substantially real-time, such that the effect of the adjustment can be viewed by a user.

FIG. 1 illustrates a user interface panel 100 used in accordance with an embodiment of the present technology. User interface panel 100 includes user control 102 configured to adjust image resolution between a maximum value and a minimum value. User interface panel 100 also includes user control 104 configured to adjust image penetration between a maximum value and a minimum value. User interface panel 100 also includes user control 106 configured to adjust frame rate between a maximum value and a minimum value. User interface panel 100 also includes user control 108 configured to adjust color flow sensitivity between a maximum value and a minimum value.

User interface panel 100 indicates that user controls 102, 104 and 106 are for use when an operably connected ultrasound imaging system is being operated in B-mode 118. User interface panel 100 indicates that user control 108 is for use when an operably connected ultrasound imaging system is being operated in color flow mode 120. In color flow mode, user controls 102, 104 and 106 can also be used, however, in B-mode, user control 108 can be disabled or removed completely from the user interface panel.

When any of user controls 102, 104, 106 and/or 108 are adjusted, corresponding scan parameters (e.g., line density, number of focal zones, frequency, dynamic range, pulse repetition frequency, number of compounding angles, etc.) can also be adjusted. User interface panel 100 is configured to display the values of such scan parameters in parameter display 110. For example, as depicted in FIG. 1, frequency 112 has a value X, dynamic range 114 has a value Y and line density 116 has a value Z. X, Y and Z represent variable numerical values that are adjusted in response to an adjustment of the imaging effects (e.g., image resolution, image penetration, frame rate and/or color flow sensitivity). In certain embodiments, displaying the corresponding scan parameter values can allow a user to learn which scan parameter values are associated with which imaging effect values.

As depicted in FIG. 1, user controls 102, 104, 106 and 108 comprise sliders provided on a graphical user interface. In certain embodiments, user controls 102, 104, 106 and 108 can comprise physical buttons, knobs, switches, trackballs and/or sliders. In certain embodiments, user controls 102, 104, 106 and 108 can comprise any form of inputs displayed on a graphical user interface, such as a menu option, for example. In certain embodiments, user controls 102, 104, 106 and 108 can comprise any form of input received at a mouse, keyboard and/or touch screen, for example.

In operation, user interface panel 100 is operably connected to a computer processor in operable communication with an image acquisition device. Inputs received at user interface panel 100 can be used by the computer processor to determine scan parameters to be used by the image acquisition device to obtain image data. The determined scan parameters can also be displayed using user interface panel 100. In certain embodiments, available user control values between the maximum and minimum are provided based on a selected value of another user control. In certain embodiments, selection of a first user control value can result in automatic selection of other user control values. In certain embodiments, the computer processor and image acquisition device can be operably connected to a display, such as a screen, for example, that is configured to display image data acquired by the image acquisition device. In certain embodiments, the display can display image data acquired by the image acquisition device in substantially real time.

Figure 2:
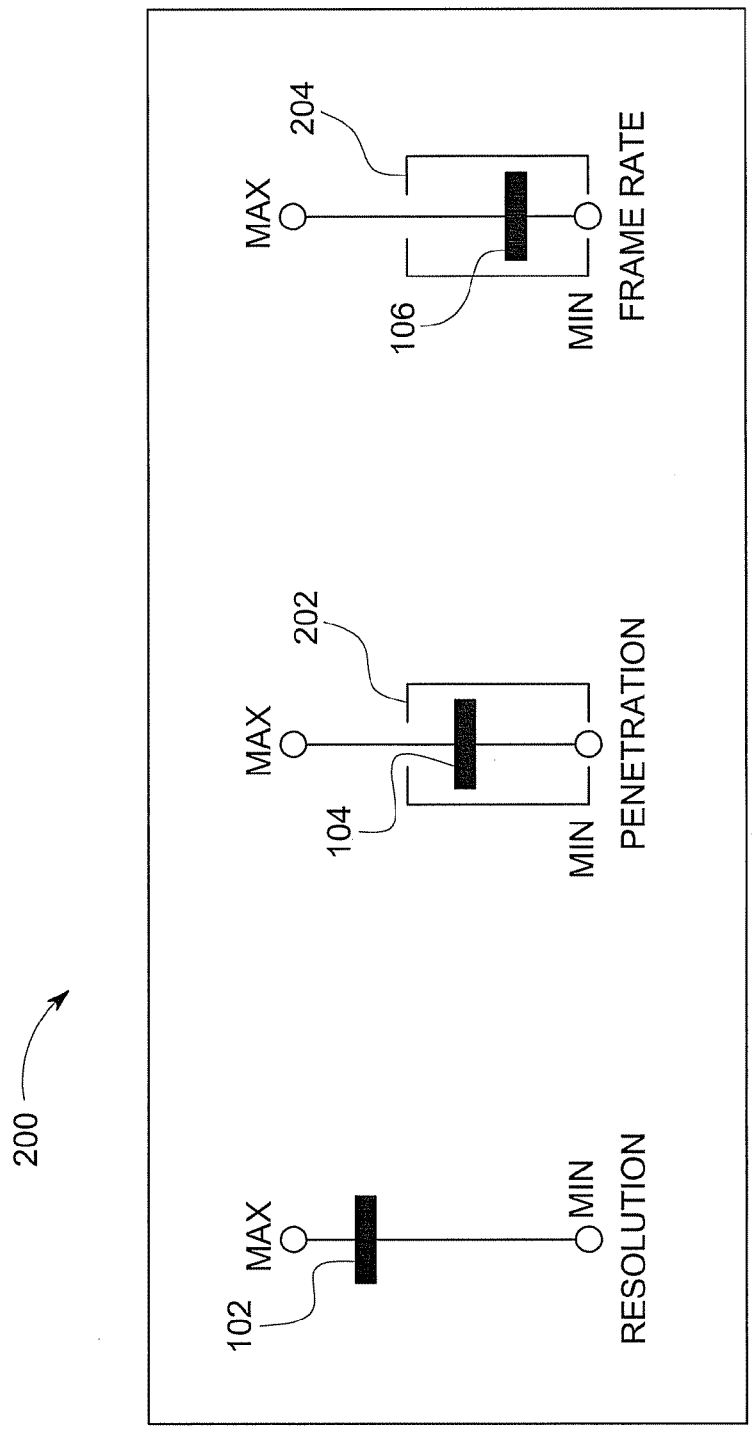
FIG. 2 illustrates a user interface panel used in accordance with an embodiment of the present technology.

FIG. 2 illustrates a user interface panel 200 used in accordance with an embodiment of the present technology. Like the user interface panel 100, user interface panel 200 includes: user control 102 configured to adjust image resolution between a maximum value and a minimum value, user control 104 configured to adjust image penetration between a maximum value and a minimum value, and user control 106 configured to adjust frame rate between a maximum value and a minimum value. User interface panel 200 also includes boundary 202 that constrains user control 104 such that the image penetration value can only be selected from within boundary 202. User interface panel 200 also includes boundary 204 that constrains user control 106 such that the frame rate value can only be selected from within boundary 204. Both boundary 202 and boundary 204 are based on the position of user control 102 and the corresponding image resolution value. In color flow imaging embodiments, the user interface panel 200 also includes a boundary that constrains user control 108 such that the color flow sensitivity value can only be selected from within the boundary.

In certain embodiments, image resolution can be set at a value and the remaining controls can be constrained by boundaries and/or automatically determined based on the set image resolution value. In certain embodiments, image penetration can be set at a value and the remaining controls can be constrained by boundaries and/or automatically determined based on the set image penetration value. In certain embodiments, frame rate can be set at a value and the remaining controls can be constrained by boundaries and/or automatically determined based on the set frame rate value. In certain embodiments, color flow sensitivity can be set at a value and the remaining controls can be constrained by boundaries and/or automatically determined based on the set color flow sensitivity value.

In certain embodiments, a radio button can be used to identify the primary imaging effect (i.e., the imaging effect that is unbounded between its minimum and maximum) such that the remaining imaging effects will be constrained based on the selected value of the primary imaging effect. In certain embodiments, the imaging effects can be ranked one through four such that the primary imaging effect (i.e., the imaging effect that is unbounded between its minimum and maximum) is ranked one, the secondary imaging effect (i.e., that is only constrained by the selected value of the primary imaging effect) is ranked two, the third imaging effect (i.e., that is only constrained by the selected values of the primary and secondary imaging effects) is ranked three, and the fourth imaging effect (i.e., that is only constrained by the selected values of the primary, secondary and third imaging effects) is ranked four. The rankings can be provided as a drop down menu in a graphical user interface or otherwise.

Figure 3:
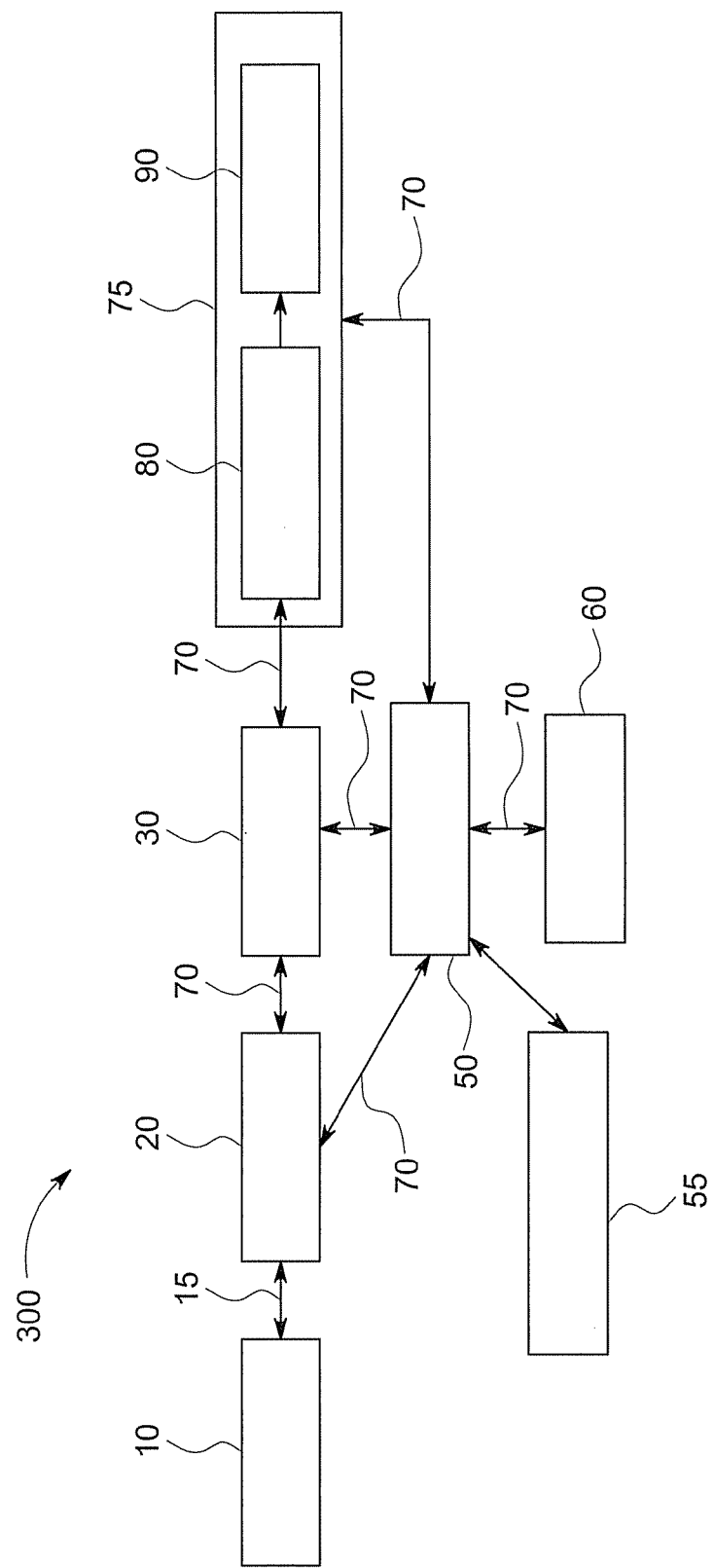
FIG. 3 illustrates a block diagram of an ultrasound imaging system used in accordance with an embodiment of the present technology.

FIG. 3 illustrates a block diagram of an ultrasound imaging system 300 used in accordance with an embodiment of the present technology. The system 100 includes a transducer 10, a front-end 20, an imaging mode processor 30, a user interface 60, a control processor 50, a data storage 55, and a display 75. In certain embodiments, the imaging mode processor 30 and the control processor 50 may be part of a back-end system.

Transducer 10 and front-end 20 can be used together to create a beam pattern that is used to create an image. Transducer 10 can be used to transmit ultrasound waves into a subject by converting electrical analog signals to ultrasonic energy. The transducer 10 can also be used to detect ultrasound waves that are backscattered from the subject by converting ultrasonic energy to analog electrical signals. In certain embodiments, the transducer 10 can be a linear array, a phased array, or any other known type of transducer.

The front-end 20 can include a receiver, a transmitter and/or a beamformer. The front-end 20 can be used to create transmitted waveforms, beam patterns, receiver filtering techniques, and demodulation schemes that can be used for various imaging modes. The front-end 20 can interface with the transducer 10 via an analog interface 15. The front-end 20 can interface with the imaging mode processor 30 and the control processor 50 via a digital bus 70. The digital bus 70 can include several digital sub-buses. The digital sub-buses can have separate configurations and provide digital data interfaces to various parts of the ultrasound imaging system 100.

Once a beam pattern has been focused, the beam pattern can be output from the front-end 20 to the imaging mode processor 30 in the form of digital signal data. The imaging mode processor 30 can process the received digital signal data to produce estimated parameter values. The imaging mode processor 30 can pass the estimated parameter values to a control processor 50 over the digital bus 70. The imaging mode processor 30 can also pass the estimated parameter values to the display 75 via the digital bus 70.

The display 75 can include a display processor 80 and a monitor 90. The display processor 80 can accept digital parameter values from the imaging mode processor 30 and the control processor 50. The display processor 80 can perform scan-conversion functions, color mapping functions, and tissue/flow arbitration functions, for example. The display processor 80 can process map and format the digital data for display, convert the digital display data to analog display signals, and pass the analog display signals to the monitor 90. The monitor 90 can accept the analog display signals from the display processor 80 and display the resulting image. An operator may view the image on the monitor 90.

The control processor 50 is the central processor of the ultrasound imaging system 100, and can comprise any processing device capable of executing computer-readable code. The control processor 50 can interface with other components of the ultrasound imaging system 300 using the digital bus 70. The control processor 50 can execute various data algorithms and functions for various imaging and diagnostic modes. Digital data and commands can be transmitted and received between the control processor 50 and other components of the ultrasound imaging system 100. In certain embodiments, functions performed by the control processor 50 can be performed by multiple processors and/or can be integrated into the imaging mode processor 30 and/or the display processor 80. In another embodiment, the functions of the processors 30, 50, and 80 can be integrated into a single personal computer ("PC") backend.

Data storage 55 can be any tangible, non-transitory computer-readable medium that is readable by processor 50, whether local, remote, connected by wires and/or connected wirelessly. For example, storage medium 55 can include a computer hard drive, a server, a CD, a DVD, a USB thumb drive, and/or any other type of tangible memory capable of storing one or more computer instructions. The sets of instructions can include one or more routines capable of being run or performed by processor 50.

The user interface 60 can allow user commands to be input by the operator to the ultrasound imaging system 300 through the control processor 50. The user interface 60 can include a keyboard, mouse, touch screen, switches, knobs, buttons, track ball, and/or on screen menus, for example.

In certain embodiments, user interface panels as described in connection with FIGS. 1 and 2 can be implemented via user interface 60 such that user interface 60 can include user controls 102, 104, 106, 108, a scan parameter display 110 and boundaries 204, 206, for example. Inputs received at user interface 60 using user interface controls 102, 104, 106 and/or 108 can be used by control processor 50 to determine scan parameters to be used by ultrasound imaging system 300 while acquiring image data. For example, control processor 50 can determine scan parameters by inputting values from user controls 102, 104, 106 and/or 108 into algorithms provided as computer-readable instructions stored in data storage 55. The determined scan parameters can then be used by ultrasound imaging system 300 while acquiring image data. In an embodiment, determined scan parameters can be used by an imaging system to acquire 2D image data and/or 3D volume data, for example.

In certain embodiments, control processor 50 can determine boundaries for user controls associated with non-primary imaging effects based on a selected value for a primary imaging effect that is selected using the user control associated with the primary imaging effect. Such boundaries can be displayed using user interface 60 and can be updated when the user control associated with the primary imaging effect is adjusted. In certain embodiments, control processor 50 can automatically determine values for user controls associated with non-primary imaging effects based on a selected value for a primary imaging effect that is selected using the user control associated with the primary imaging effect.

Figure 4:
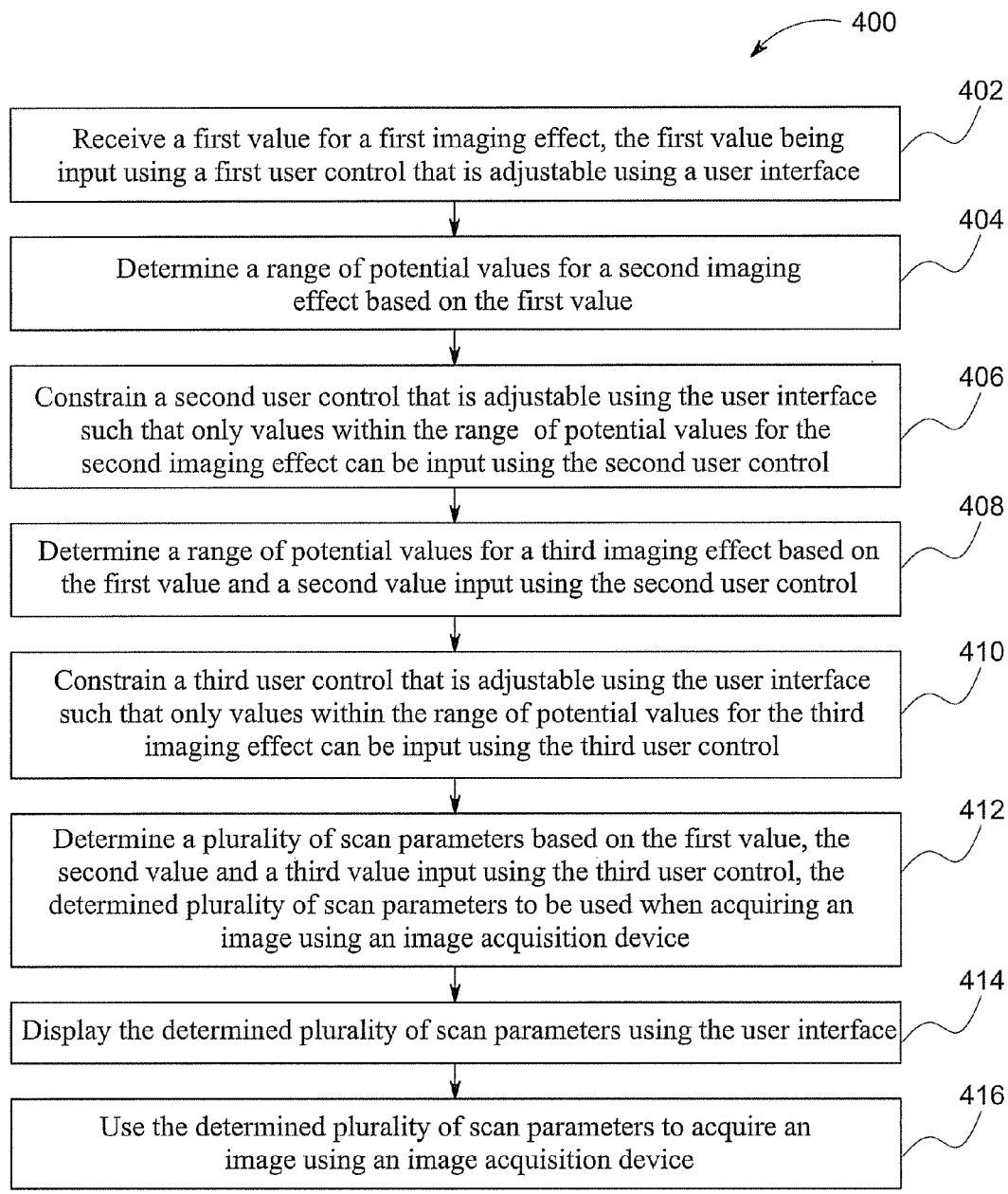
FIG. 4 illustrates a method for determining scan parameters to be used during image acquisition used in accordance with an embodiment of the present technology.

FIG. 4 illustrates a method 400 for determining scan parameters to be used during image acquisition used in accordance with an embodiment of the present technology. The method can be applied by employing the techniques and systems described herein.

At 402, a first value for a first imaging effect is received, the first value being input using a first user control that is adjustable using a user interface. For example, in an embodiment, a processor operably connected to an ultrasound imaging system and a user interface can receive a first value for a first imaging effect, the first value being input using a first user control that is adjustable using the user interface. In an embodiment, an imaging effect can be one of the following: image resolution, image penetration, frame rate or color flow sensitivity.

At 404, a range of potential values for a second imaging effect is determined based on the first value. For example, in an embodiment, a processor operably connected to an ultrasound imaging system and a user interface can determine a range of potential values for a second imaging effect based on the first value.

At 406, a second user control that is adjustable using the user interface is constrained such that only values within the range of potential values for the second imaging effect can be input using the second user control. For example, in an embodiment, a processor operably connected to an ultrasound imaging system and a user interface can constrain a second user control that is adjustable using the user interface such that only values within the range of potential values for the second imaging effect can be input using the second user control.

At 408, a range of potential values for a third imaging effect is determined based on the first value and a second value input using the second user control. For example, in an embodiment, a processor operably connected to an ultrasound imaging system and a user interface can determine a range of potential values for a third imaging effect based on the first value and a second value input using the second user control.

At 410, a third user control that is adjustable using the user interface is constrained such that only values within the range of potential values for the third imaging effect can be input using the third user control. For example, in an embodiment, a processor operably connected to an ultrasound imaging system and a user interface can constrain a third user control that is adjustable using the user interface such that only values within the range of potential values for the third imaging effect can be input using the third user control.

At 412, a plurality of scan parameters is determined based on the first value, the second value and a third value input using the third user control, the determined plurality of scan parameters to be used when acquiring an image using an image acquisition device. For example, in an embodiment, a processor operably connected to an ultrasound imaging system and a user interface can determine a plurality of scan parameters based on the first value, the second value and a third value input using the third user control, the determined plurality of scan parameters to be used when acquiring an image using the ultrasound imaging system. In an embodiment, the plurality of scan parameters can include one or more of the following: line density, number of focal zones, frequency, dynamic range, pulse repetition frequency, number of compounding angles.

At 414, the determined plurality of scan parameters are displayed using the user interface. For example, in an embodiment, a processor operably connected to a user interface can use the user interface to display the determined plurality of scan parameters.

At 416, the determined plurality of scan parameters are used to acquire an image using an image acquisition device. For example, in an embodiment, a processor operably connected to an ultrasound imaging system can use the ultrasound imaging system to acquire an image using the determined plurality of scan parameters. In an embodiment, determined scan parameters can be used by an imaging system to acquire 2D image data and/or 3D volume data, for example.

Certain embodiments of the present invention may omit one or more of the steps and/or perform the steps in a different order than the order listed in connection with FIG. 4. For example, some steps may not be performed in certain embodiments of the present invention. As a further example, certain steps may be performed in a different temporal order, including simultaneously, than listed above.

One or more of the steps of the method 400 may be implemented alone or in combination in hardware, firmware, and/or as a set of instructions in software, for example. Certain embodiments may employ the ultrasound imaging system 300 described herein including processor 50 to achieve the method steps. Certain embodiments may employ user interface controls 100, 200 described herein to achieve the method steps.

Figure 5:
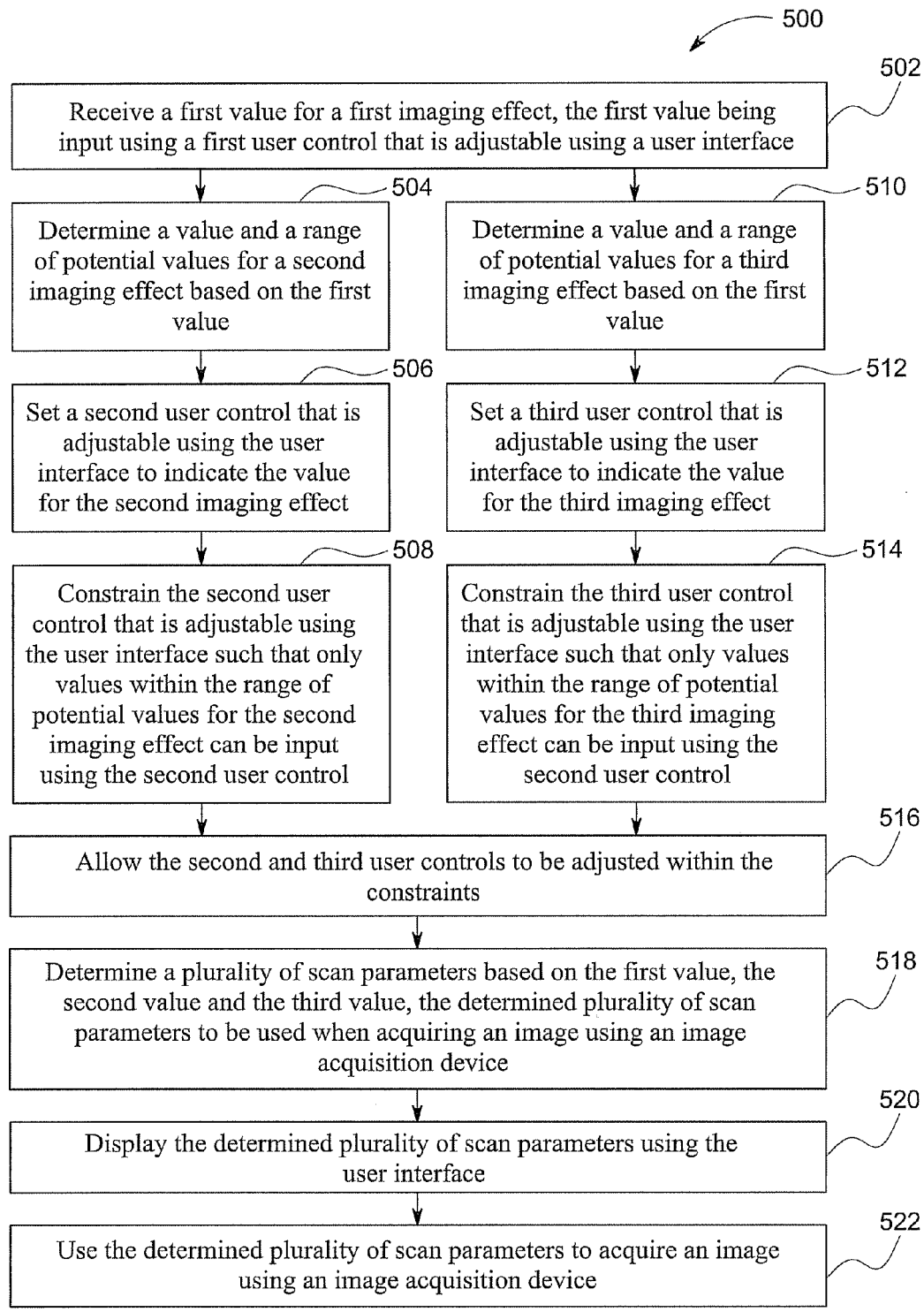
FIG. 5 illustrates a method for determining scan parameters to be used during image acquisition used in accordance with an embodiment of the present technology.

FIG. 5 illustrates a method 400 for determining scan parameters to be used during image acquisition used in accordance with an embodiment of the present technology. The method can be applied by employing the techniques and systems described herein.

At 502, a first value for a first imaging effect is received, the first value being input using a first user control that is adjustable using a user interface. For example, in an embodiment, a processor operably connected to an ultrasound imaging system and a user interface can receive a first value for a first imaging effect, the first value being input using a first user control that is adjustable using the user interface. In an embodiment, an imaging effect can be one of the following: image resolution, image penetration, frame rate or color flow sensitivity.

At 504, a value and a range of potential values for a second imaging effect is determined based on the first value. For example, in an embodiment, a processor operably connected to an ultrasound imaging system and a user interface can determine a value and a range of potential values for a second imaging effect based on the first value.

At 506, a second user control that is adjustable using the user interface is set to display the value of the second imaging effect. For example, in an embodiment, a processor operably connected to an ultrasound imaging system and a user interface can set a second user control that is adjustable using the user interface to display the value of the second imaging effect.

At 508, the second user control is constrained such that only values within the range of potential values for the second imaging effect can be input using the second user control. For example, in an embodiment, a processor operably connected to an ultrasound imaging system and a user interface can constrain a second user control that is adjustable using the user interface such that only values within the range of potential values for the second imaging effect can be input using the second user control.

At 510, a value and a range of potential values for a third imaging effect is determined based on the first value. For example, in an embodiment, a processor operably connected to an ultrasound imaging system and a user interface can determine a value and a range of potential values for a third imaging effect based on the first value.

At 512, a third user control that is adjustable using the user interface is set to display the value of the third imaging effect. For example, in an embodiment, a processor operably connected to an ultrasound imaging system and a user interface can set a third user control that is adjustable using the user interface to display the value of the third imaging effect.

At 514, the third user control is constrained such that only values within the range of potential values for the third imaging effect can be input using the second user control. For example, in an embodiment, a processor operably connected to an ultrasound imaging system and a user interface can constrain a third user control that is adjustable using the user interface such that only values within the range of potential values for the third imaging effect can be input using the third user control.

At 516, the second and third user controls are allowed to be adjusted within the constraints. For example, in an embodiment, a processor operably connected to an ultrasound imaging system and a user interface can: (1) receive a second value for a second imaging effect, the second value being input using the second user control, and the second value being within the range of potential values for the second imaging effect; and (2) receive a third value for a third imaging effect, the third value being input using the third user control, and the third value being within the range of potential values for the third imaging effect.

At 518, a plurality of scan parameters is determined based on the first value, the second value and the third value, the determined plurality of scan parameters to be used when acquiring an image using an image acquisition device. For example, in an embodiment, a processor operably connected to an ultrasound imaging system and a user interface can determine a plurality of scan parameters based on the first value, the second value and the third value, the determined plurality of scan parameters to be used when acquiring an image using the ultrasound imaging system. In an embodiment, the plurality of scan parameters can include one or more of the following: line density, number of focal zones, frequency, dynamic range, pulse repetition frequency, number of compounding angles.

At 520, the determined plurality of scan parameters are displayed using the user interface. For example, in an embodiment, a processor operably connected to a user interface can use the user interface to display the determined plurality of scan parameters.

At 522, the determined plurality of scan parameters are used to acquire an image using an image acquisition device. For example, in an embodiment, a processor operably connected to an ultrasound imaging system can use the ultrasound imaging system to acquire an image using the determined plurality of scan parameters. In an embodiment, determined scan parameters can be used by an imaging system to acquire 2D image data and/or 3D volume data, for example.

Certain embodiments of the present invention may omit one or more of the steps and/or perform the steps in a different order than the order listed in connection with FIG. 5. For example, some steps may not be performed in certain embodiments of the present invention. As a further example, certain steps may be performed in a different temporal order, including simultaneously, than listed above.

One or more of the steps of the method 500 may be implemented alone or in combination in hardware, firmware, and/or as a set of instructions in software, for example. Certain embodiments may employ the ultrasound imaging system 300 described herein including processor 50 to achieve the method steps. Certain embodiments may employ user interface controls 100, 200 described herein to achieve the method steps.

Certain embodiments of the present technology can be provided as a set of instructions residing on a tangible, non-transitory computer-readable medium, such as a memory, hard disk, DVD, or CD, for execution on a general purpose computer or other processing device. For example, certain embodiments provide a non-transitory computer-readable storage medium encoded with a set of instructions for execution on a processing device and associated processing logic, wherein the set of instructions includes a routine(s) configured to provide the functions described in connection with the systems and methods described herein.

Applying systems and techniques described herein, can provide a technical effect of selecting multiple scan parameters to be used during image acquisition based on an input value for a desired imaging effect, such as image resolution, image penetration, frame rate, and/or color flow sensitivity, for example.

Certain image data acquired, analyzed and displayed in connection with techniques described herein represent human anatomy. In other words, outputting a visual display based on such data comprises a transformation of underlying subject matter (such as an article or materials) to a different state.

While the invention has been described with reference to embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. A method for determining scan parameters to be used during image acquisition comprising:
   receiving a first value for a first imaging effect, the first value being input using a first user control that is adjustable using a user interface;
   using the computer processor to separately determine a second value for a second imaging effect based on the first value for the first imaging effect; and
   using a computer processor to determine a plurality of scan parameters based at least on the first value, the determined plurality of scan parameters to be used when acquiring an image using an image acquisition device.

2. The method of claim 1, wherein the plurality of scan parameters includes one or more of the following: line density, number of focal zones, frequency, dynamic range, pulse repetition frequency, number of compounding angles.

3. The method of claim 1, wherein the first imaging effect is one of the following: image resolution, image penetration, frame rate or color flow sensitivity.

4. The method of claim 1, further comprising displaying the determined plurality of scan parameters using the user interface.

5. The method of claim 1, further comprising:
   using the computer processor to determine a third value for a third imaging effect based on the first value.

6. A system for determining scan parameters to be used during image acquisition comprising:
   a computer processor configured to:
   receive a first value for a first imaging effect, the first value being input using a first user control that is adjustable using a user interface that is operably connected to the computer processor,
   separately determine a value for a second imaging effect based on the first value for the first imaging effect, and
   determine a plurality of scan parameters based at least on the first value, the determined plurality of scan parameters to be used when acquiring an image using an image acquisition device.

7. The system of claim 6, wherein the plurality of scan parameters includes one or more of the following: line density, number of focal zones, frequency, dynamic range, pulse repetition frequency, number of compounding angles.

8. The system of claim 6, wherein the first imaging effect is one of the following: image resolution, image penetration, frame rate or color flow sensitivity.

9. The system of claim 6, wherein the image acquisition device is an ultrasound imaging system.

10. The system of claim 6, wherein the computer processor is configured to determine a value for a third imaging effect based on the first value.

11. A non-transitory computer-readable storage medium encoded with a set of instructions for execution on a processing device and associated processing logic, wherein the set of instructions includes:
- a first routine configured to receive a first value for a first imaging effect, the first value being input using a first user control that is adjustable using a user interface;
- a second routine configured to separately determine a second value for a second imaging effect based on the first value for the first imaging effect; and
- a third routine configured to determine a plurality of scan parameters based at least on the first value, the determined plurality of scan parameters to be used when acquiring an image using an image acquisition device.

\* \* \* \* \*

UNITED STATES PATENT AND TRADEMARK OFFICE
CERTIFICATE OF CORRECTION

PATENT NO. : 8,526,669 B2  
APPLICATION NO. : 12/906703  
DATED : September 3, 2013  
INVENTOR(S) : Brent Jason Lavin and Menachem Halmann It is certified that error appears in the above-identified patent and that said Letters Patent is hereby corrected as shown below:

In the Claims

In col. 12, line 31, claim 1, after the word "using" delete "the" and substitute therefor --a--;

In col. 12, line 34, claim 1, after the word "using" delete "a" and substitute therefor --the--.

Signed and Sealed this  
Twelfth Day of November, 2013

Teresa Stanek Rea  
*Deputy Director of the United States Patent and Trademark Office*